(12) United States Patent
Gordon et al.

(10) Patent No.: US 8,297,972 B2
(45) Date of Patent: Oct. 30, 2012

(54) COMBINATION TONGUE AND FLAP RETRACTOR

(75) Inventors: Manuel Barry Gordon, New York, NY (US); Matthew Gordon, Hastings On Hudson, NY (US)

(73) Assignee: Manuel Barry Gordon, New York, NY (US)

( * ) Notice: Subject to any disclaimer, the term of this patent is extended or adjusted under 35 U.S.C. 154(b) by 536 days.

(21) Appl. No.: 12/405,751

(22) Filed: Mar. 17, 2009

(65) Prior Publication Data

US 2010/0240005 A1  Sep. 23, 2010

(51) Int. Cl.
*A61C 3/00* (2006.01)
*A61C 17/10* (2006.01)
*A61B 1/24* (2006.01)

(52) U.S. Cl. ............................ 433/140; 600/237; 433/93

(58) Field of Classification Search .............. 433/91–96, 433/140, 141; 600/237–242, 205, 210; 604/902
See application file for complete search history.

(56) References Cited

U.S. PATENT DOCUMENTS

| | | | | |
|---|---|---|---|---|
| 1,465,259 A * | 8/1923 | Friedman | | 600/227 |
| 1,497,749 A * | 6/1924 | Diack | | 433/144 |
| 2,603,870 A * | 7/1952 | Nordin | | 433/93 |
| 3,090,122 A * | 5/1963 | Erickson | | 433/93 |
| 4,270,902 A * | 6/1981 | Wiland | | 433/144 |
| 4,883,426 A * | 11/1989 | Ferrer | | 433/91 |
| 5,078,602 A * | 1/1992 | Honoshofsky | | 433/91 |
| 5,846,192 A * | 12/1998 | Teixido | | 600/210 |
| 6,174,162 B1 * | 1/2001 | Pozzi | | 433/3 |
| 6,241,658 B1 * | 6/2001 | Goodrich | | 600/210 |
| 6,575,749 B1 * | 6/2003 | Greenwald | | 433/141 |
| 7,238,023 B1 * | 7/2007 | Enos | | 433/91 |
| 2002/0128673 A1 * | 9/2002 | Ripich et al. | | 606/161 |
| 2005/0228233 A1 * | 10/2005 | Ritland | | 600/210 |

OTHER PUBLICATIONS

Instruments-Miscellaneous, Knives/Spatulas/Retractors, Sullivan-Schein Dental Supply Catalog, 2007, p. 584.
Instruments-Retractors, Misch Spoon and Minesota Retractor, Salvin Dental Supply Catalog, 2011, p. 114.

* cited by examiner

*Primary Examiner* — Todd Manahan
*Assistant Examiner* — Michael R Ballinger
(74) *Attorney, Agent, or Firm* — Stroock & Stroock & Lavan LLP

(57) ABSTRACT

A combination retractor includes an operational unit, a neck region and a handle region. The operational unit further includes a tongue retractor and a flap retractor. The tongue retractor may be concave to provide for a natural area to encapsulate the tongue. The tongue and flap retractors may also be provided as part of a continuous planar extension of the operational unit or may be disposed on different planes. The flap retractor may be formed of a tapered extended edge or tab, which can be made in various lengths and include a beveled edge. A suction mechanism may be added for eliminating fluids. The neck region may contain an S-shaped bend or lateral bends for better operative functionality and ergonomics. The proximal end of the handle region, opposite the operational unit, may further include any useful apparatus, such as a periosteal elevator or periosteal retractor.

17 Claims, 20 Drawing Sheets

310

510

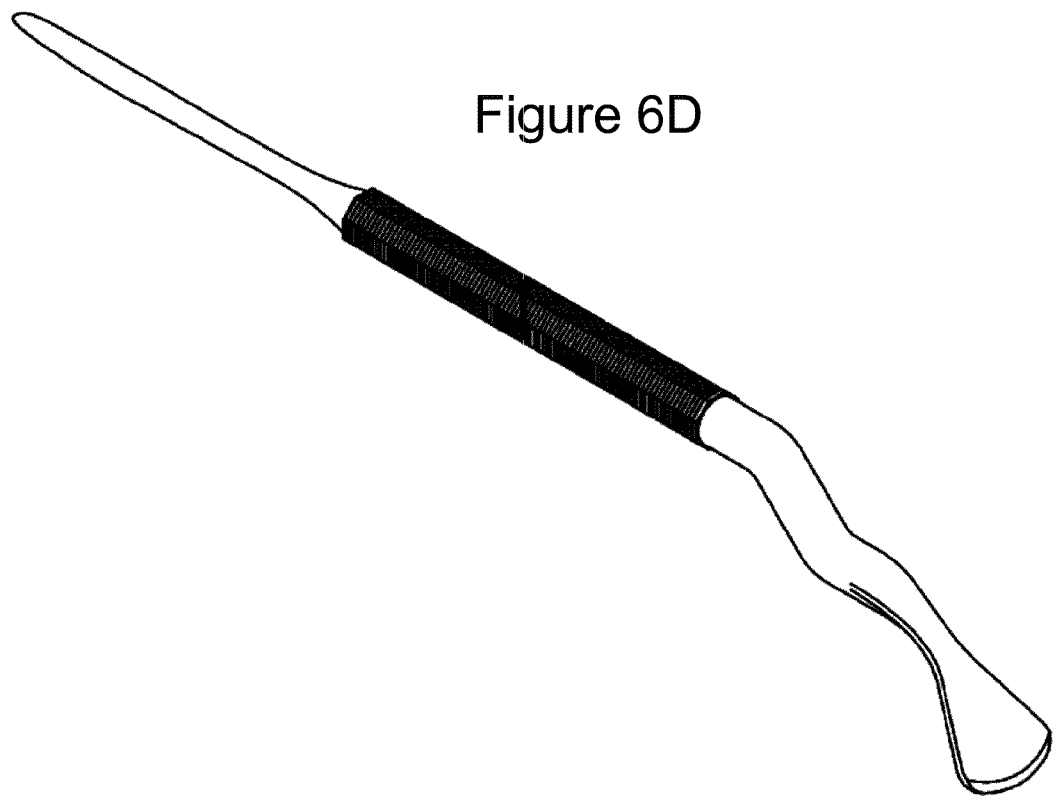
Figure 6D
Figure 6E
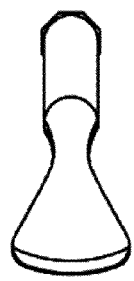
Figure 6F
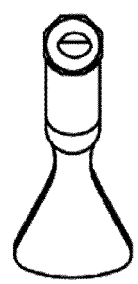

716

810

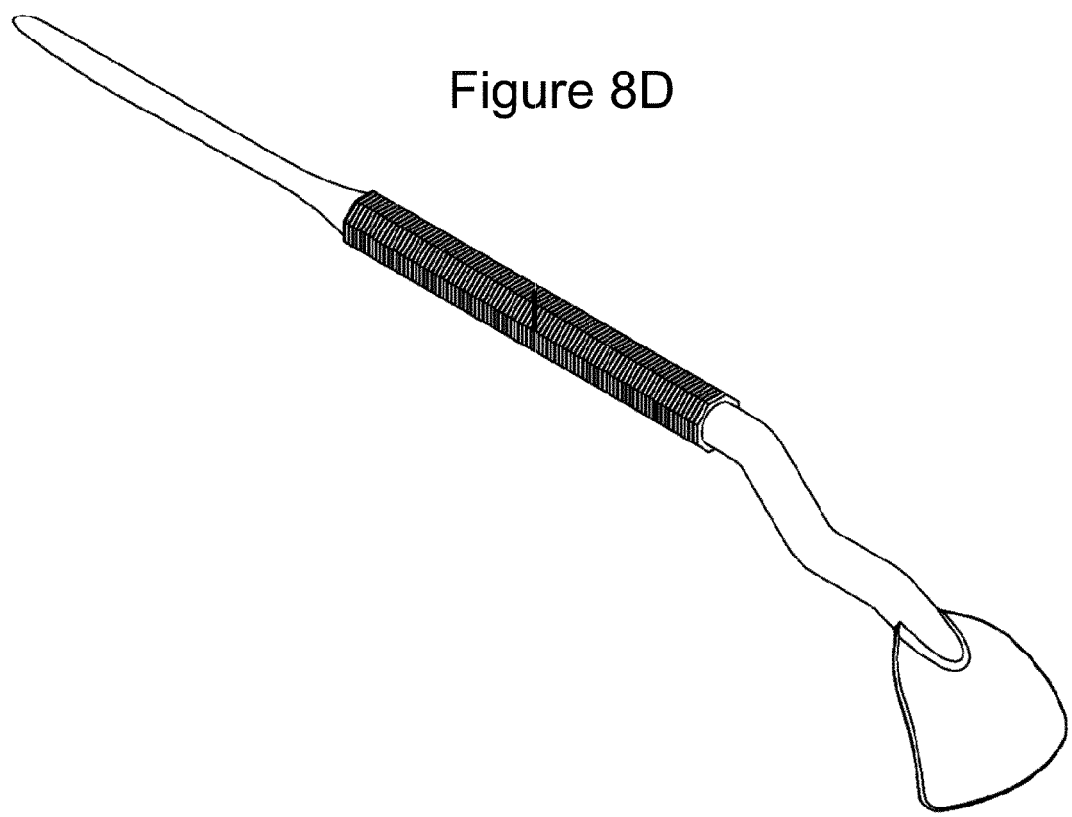
Figure 8D
Figure 8E
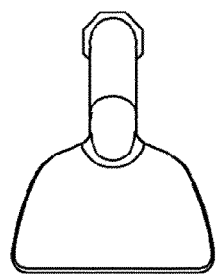
Figure 8F
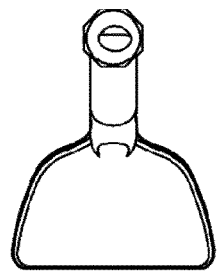

910

914

914

COMBINATION TONGUE AND FLAP RETRACTOR

FIELD OF THE INVENTION

The present invention generally relates to the fields of general dentistry, oral surgery and periodontal surgery and to surgical instrumentation used therein. More specifically, the invention relates to a combination tongue and flap retractor and a distinct tongue retractor for use in general dental procedures, periodontal and oral surgery.

BACKGROUND OF THE INVENTION

Many dental procedures require the precise use of surgical instruments within a small and restricted area of operation. Furthermore, it is usually desirable to selectively supply air or water to a treatment area, drill in a treatment area, or to manipulate soft tissue. To do so, practitioners have conventionally used various instruments to manipulate tissue, suction liquids or retract the tongue while performing the desired procedure.

Conventional methods, however, present several problems. First, because of the restricted area, it is undesirable and usually impractical to crowd the oral cavity with multiple instruments. When two or three different instruments are placed in a patient's oral cavity, the practitioner is unable to clearly see the area of operation. Furthermore, because of the tight quarters, the instruments become limited in their range of motion. Thus, the degree of difficulty is unnecessarily increased for even the simplest of procedures.

Furthermore, the use of multiple instruments is impractical as it severely limits the ability of the dentist, periodontist, oral surgeon or assistant (herein, "Dentist") to properly perform the required procedures. For instance if a Dentist uses one hand to retract the tongue and another to hold a surgical flap away from the treatment area, then he will need to ask for an assistant to reach for another instrument, or the assistant must hold an instrument and retract either the tongue or flap while he/she is simultaneously suctioning or performing a different task. The only other option would be to perform the operation in segments or go back and forth between instruments until the procedure is complete. This unnecessary complexity lengthens the time of operation, reduces the efficiency of the procedure and increases patient discomfort.

Finally, a common problem in the field is that dentists regularly complain of neck, back, shoulder pain and carpal tunnel syndrome related hand pain. In fact, a comprehensive literature search indicates dental care providers are at high risk for suffering a workplace musculoskeletal disorder (WMSD) and neuromuscular disorders, e.g. disc herniation. Studies have reported that dental workers who suffer a WMSD injury have a lost work day average of 93 days per incident. In fact, sixty-two percent of dental hygienists have complained of neck problems and eighty-one percent have complained of shoulder pain in one or both shoulders. Studies have also shown that between six and seven percent of all dental hygienists report being diagnosed with carpal tunnel syndrome and that fifty-nine percent of dentists have reported musculoskeletal pain. A survey of a U.S. Army dental clinic reported that over seventy-five percent of all dental workers complained of one or more carpal tunnel syndrome symptoms, over fifty percent complained of back and shoulder pain, and eleven percent were diagnosed as having carpal tunnel syndrome. These disorders and others can be addressed with proper emphasis on ergonomics and posture, and by shortening the length of the dental procedure.

Thus, missing from the art is an invention that allows greater control, while affording the Dentist an opportunity to practice with better posture. Moreover, an invention that reduces the time of operation would have several benefits for both patients and practitioners: (i) reducing the strain on the neck, back, shoulders and hands of Dentists, (ii) reducing the amount of discomfort experienced by patients during procedures in which they remain awake, and (iii) reducing the adverse risks to the patient associated with the use of general anesthesia in situations where patients are put to sleep for a procedure.

SUMMARY OF THE INVENTION

The present invention, in one embodiment, is directed to a combination tongue and surgical flap retractor. The combination retractor may include an operational unit, a neck region and a handle region. The operational unit further includes a tongue retractor and a flap retractor. The tongue retractor may be formed with a concave shape or with an increased overall thickness of the operational unit. The flap retractor may be formed with a tapered extended edge or tab, which can be made in various lengths. Furthermore, the flap retractor may also include a beveled edge. The combination retractor may be formed in a way such that the tongue retractor is disposed on a different plane than the flap retractor. The retractor may also include a suction mechanism for eliminating fluids such as saliva, water, and blood from the oral cavity.

The present invention is also directed to improved ergonomics in the neck region of the combination retractor, the non-combination tongue retractor and in the suction device embodiments. In one embodiment, the neck region contains an S-shaped design for better ergonomics. Furthermore, the neck region may also include a lateral bend positioned at the proximal end of the operational unit, so as to position the operational unit either to the right or the left with respect to the central axis of the handle. Therefore, this facilitates specific use on a respective side of the mouth based on the direction of the lateral bend.

Finally, the present invention is directed to improvements in the handle region of the combination retractor. In one embodiment, the handle region includes a grip portion. The proximal end of the handle region may further include a dental pick, a dental probe, a dental hook, a periosteal elevator, or a periosteal retractor or any other dental instrument.

Other features and advantages of the present invention will become more fully apparent and understood with reference to the following description, the accompanying drawings and the appended claims.

BRIEF DESCRIPTION OF THE FIGURES

These and other objects and features of the invention will become more apparent by referring to the drawings, in which:

FIG. 1b is a side elevation view of the combination retractor shown in FIG. 1a;

FIG. 1c is a top view of the combination retractor shown in FIG. 1a;

FIG. 1d is a perspective view of the combination retractor shown in FIG. 1a;

FIG. 1e is a top plan view of the operational unit of the combination retractor shown in FIG. 1a;

FIG. 1f is a bottom plan view of the operational unit of the combination retractor shown in FIG. 1a;

FIG. 2b is a side elevation view of the combination retractor shown in FIG. 2a;

FIG. 2c is a top view of the combination retractor shown in FIG. 2a;

FIG. 2d is a perspective view of the combination retractor shown in FIG. 2a;

FIG. 2e is a top plan view of the operational unit of the combination retractor shown in FIG. 2a;

FIG. 2f is a bottom plan view of the operational unit of the combination retractor shown in FIG. 2a;

FIG. 3b is a side elevation view of the combination retractor shown in FIG. 3a;

FIG. 3c is a top view of the retractor shown in FIG. 3a;

FIG. 3d is a perspective view of the combination retractor shown in FIG. 3a;

FIG. 3e is a top plan view of the operational unit of the combination retractor shown in FIG. 3a;

FIG. 3f is a bottom plan view of the operational unit of the combination retractor shown in FIG. 3a;

FIG. 4b is a side elevation view of the combination retractor shown in FIG. 4a;

FIG. 4c is a top view of the combination retractor shown in FIG. 4a;

FIG. 4d is a perspective view of the combination retractor shown in FIG. 4a;

FIG. 4e is a top plan view of the operational unit of the combination retractor shown in FIG. 4a;

FIG. 4f is a bottom plan view of the operational unit of the combination retractor shown in FIG. 4a;

FIG. 5b is a side elevation view of the combination retractor shown in FIG. 5a;

FIG. 5c is a top view of the combination retractor shown in FIG. 5a;

FIG. 5d is a perspective view of the combination retractor shown in FIG. 5a;

FIG. 5e is a top plan view of the operational unit of the combination retractor shown in FIG. 5a;

FIG. 5f is a bottom plan view of the operational unit of the combination retractor shown in FIG. 5a;

FIG. 6b is a side elevation view of the combination retractor shown in FIG. 6a;

FIG. 6c is a top view of the combination retractor shown in FIG. 6a;

FIG. 6d is a perspective view of the combination retractor shown in FIG. 6a;

FIG. 6e is a top plan view of the operational unit of the combination retractor shown in FIG. 6a;

FIG. 6f is a bottom plan view of the operational unit of the combination retractor shown in FIG. 6a;

FIG. 7b is a side elevation view of the combination retractor shown in FIG. 7a;

FIG. 7c is a top view of the combination retractor shown in FIG. 7a;

FIG. 7d is a perspective view of the combination retractor shown in FIG. 7a;

FIG. 7e is a top plan view of the operational unit of the combination retractor shown in FIG. 7a;

FIG. 7f is a bottom plan view of the operational unit of the combination retractor shown in FIG. 7a;

FIG. 8b is a side elevation view of the combination retractor shown in FIG. 8a;

FIG. 8c is a top view of the combination retractor shown in FIG. 8a;

FIG. 8d is a perspective view of the combination retractor shown in FIG. 8a;

FIG. 8e is a top plan view of the operational unit of the combination retractor shown in FIG. 8a;

FIG. 8f is a bottom plan view of the operational unit of the combination retractor shown in FIG. 8a;

FIG. 9b is a side elevation view of the combination retractor shown in FIG. 9a;

FIG. 9c is a top view of the combination retractor shown in FIG. 9a;

FIG. 9d is a perspective view of the combination retractor shown in FIG. 9a;

FIG. 9e is a top plan view of the operational unit of the combination retractor shown in FIG. 9a;

FIG. 9f is a bottom plan view of the operational unit of the combination retractor shown in FIG. 9a;

FIG. 10b is a side elevation view of the combination retractor shown in FIG. 10a;

FIG. 10c is a top view of the combination retractor shown in FIG. 10a;

FIG. 10d is a perspective view of the combination retractor shown in FIG. 10a;

FIG. 10e is a top plan view of the operational unit of the combination retractor shown in FIG. 10a;

FIG. 10f is a bottom plan view of the operational unit of the combination retractor shown in FIG. 10a;

DETAILED DESCRIPTION OF ILLUSTRATIVE EMBODIMENTS

Figure 1A:
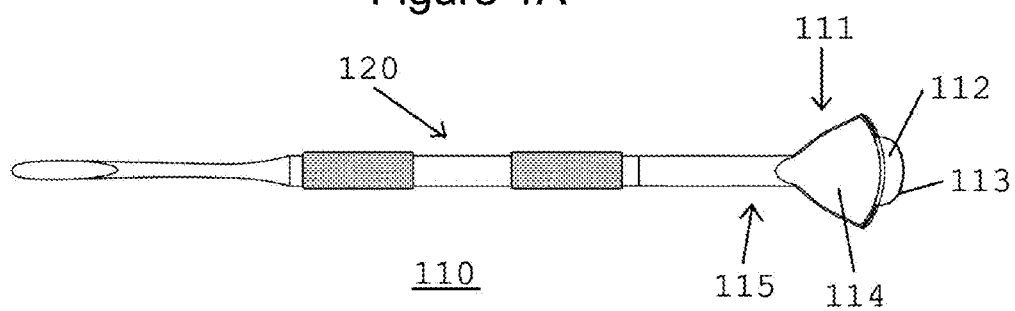
FIG. 1a is a bottom elevation view of a combination tongue and flap retractor with an S-shaped bend in accordance with an embodiment of the present invention.

Referring now to the drawings, FIG. 1a shows a combination tongue and flap retractor 110 according to one embodiment of the present invention. The combination retractor 110 may be formed of stainless steel, carbide, plastic or resin, or any other alloy or combination as is known in the art, and may include an operational unit 111, a neck region 115 and a handle region 120. Furthermore, the combination retractor may also be disposable.

The combination tongue and flap retractor may be formed so as to be hollow or solid in construction. Additionally, the retractor may be partially hollow and/or partially solid in construction, i.e., some portions of the retractor may be hollow and some portions may be solid. Additionally, the cross section of the various portions of the combination tongue and flap retractor may be in different shapes. For example, the retractor may be round in cross section, or it could be faceted, such as for example a six-sided hexagon, an eight-sided octagon, and the like. Additionally, portions of the retractor may have different cross sections. For example, one portion of the retractor may be round in cross section, while another portion of the retractor may be faceted.

The operational unit 111 may further include a flap retractor 112 at the distal end of the instrument. This flap retractor 112 preferably has a beveled edge 113, which allows the flap retractor 112 to more easily hold the flap away from the treatment area. The operational unit 111 may further contain a concave tongue retractor 114 for retracting the tongue away from the treatment area where the Dentist is working. The concave tongue retractor 114 is used to retract and/or isolate the tongue during a procedure. The tongue retractor 114 differs from conventional instruments in terms of functional shape and size. As can be appreciated from FIG. 1b, the concave tongue retractor 114 is preferably shaped to provide for a natural area to encapsulate the tongue, thereby removing it from the treatment area.

Thus, the design of the flap retractor 112 makes it useful for reflecting a soft tissue flap (the gingival and/or gingival mucosa that has been raised as a surgical flap on the lingual aspect of the mandible). The combination retractor 110 may be used to perform both functions at once or perform each function, e.g., tongue retraction and flap retraction, either simultaneously or separately depending on the Dentist's need. Combining these functions into a single device eliminates the need for two separate devices in the oral cavity during procedures, frees up a hand of the Dentist for other potential uses or eliminates the need to have an assistant's hand in the treatment area, and shortens the time of operation.

The present invention provides improved ergonomics through the use of S-shapes and bends, which allow the instruments to be used on different sides of the mandible. These ergonomic features can be optionally incorporated into each of the devices discussed herein. In one embodiment, the neck region 115 may contain an S-shape bend 117. The S-shape allows the device to align more optimally in the oral cavity, such that a greatly reduced amount of downward and/or lateral force is needed to effect the desired tongue or flap retraction as compared to conventional instruments. This dramatically decreases the Dentist's fatigue and discomfort, and avoids prolonged strain on the neck, shoulder, back, and hand, thus reducing the risk of injury to the Dentist.

Figure 1B:
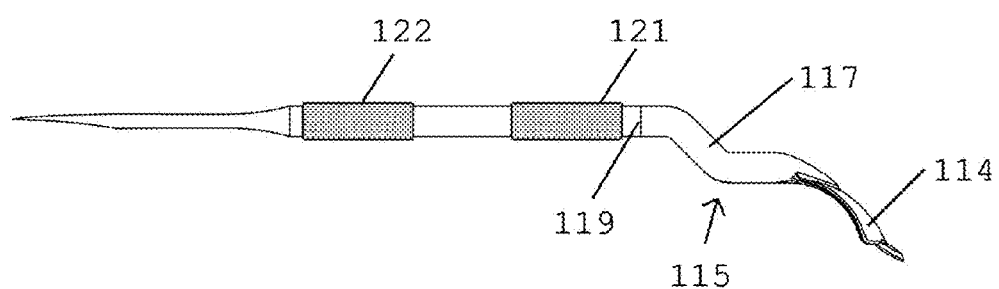

As illustrated in FIG. 1b, the neck region 115 of the combination tongue and flap retractor of the present invention may further include a thread 119 for connecting the retractor to the handle 120. The thread 119, located at the end of the neck region 115, serves to connect the neck region to the handle region 120. Additionally, any other method used in the art may be used for connecting the two places. Alternatively, the combination tongue and flap retractor may also be formed as a unitary, one-piece implement in which case threads or other attachment mechanisms would not be needed.

Figure 1C:
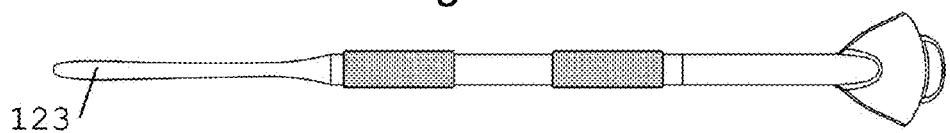
Figure 1D:
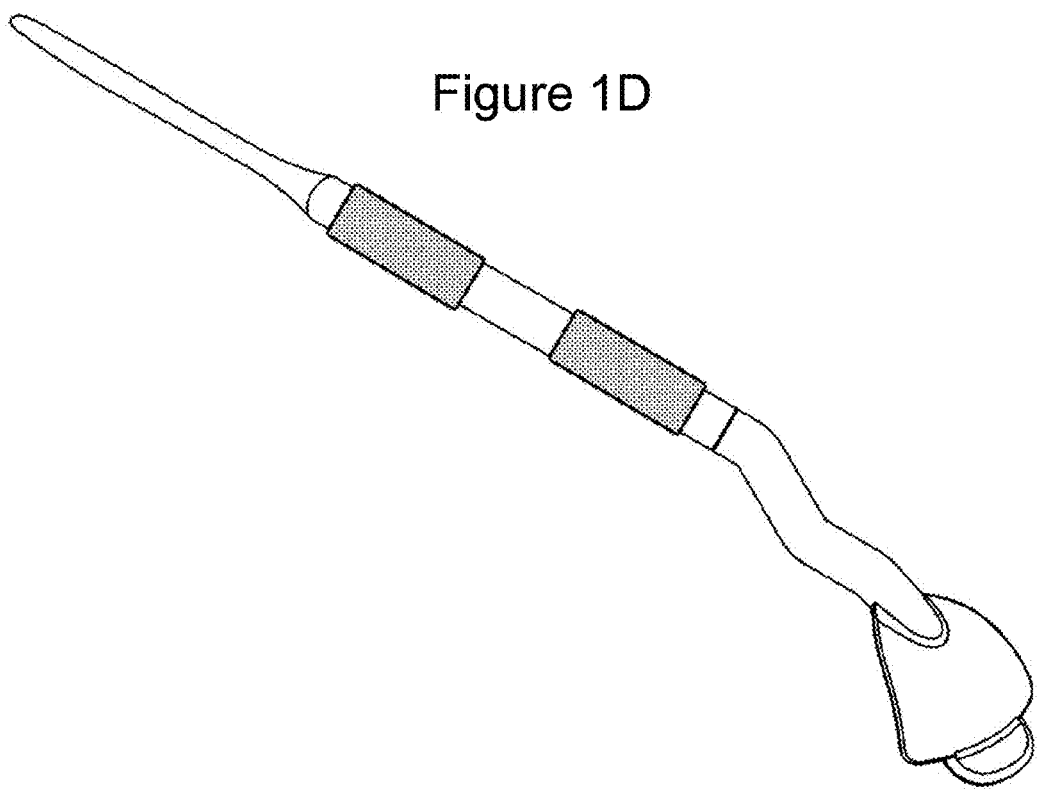
Figure 1E:
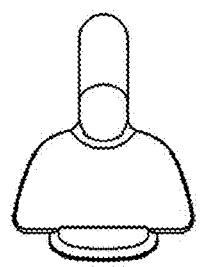
Figure 1F:
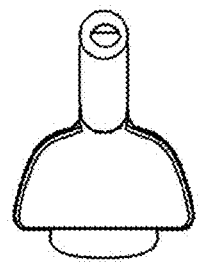

In one embodiment, the handle 120 may include grip portions 121 and 122. These grip portions provide the practitioner with a comfortable, yet sure grip as he manipulates the instrument. The grip portions 121 and 122 may be located at various positions along the handle 120 as desired for a comfortable grip. Further, the grip portions may be discrete, separate grip portions, or alternatively, a single grip portion may be provided on the retractor. In one embodiment the grip portions 121 and 122 may be constructed with an embossed pattern. This embossing may be in the form of ribs, raised dots, or the like, or may also be constructed of a separate grip mat made of plastic, rubber or any other suitable material. As shown in FIG. 1c, in one embodiment the proximal end of the handle may optionally include another dental instrument, such as a periosteal elevator 123. Furthermore, as can be appreciated by those skilled in the art, the proximal end of the handle 120 may instead include a dental probe, a dental hook, or other useful apparatus.

In another embodiment the tongue portion of the combination retractor may be longer and more sharply curved, i.e., having a curved profile. This embodiment, shown in FIGS. 2a-2f, has a tongue retractor 214 with an increased concavity (see FIG. 2b) for better encapsulation of the tongue and/or better accommodation of patients with larger tongues. The concave tongue and flap retractor 210 may be formed by sharply curving the distal portion of the tongue retractor 214, such that when viewed from the side, the tongue retractor 214 is substantially nonlinear and curved in profile.

Figure 2A:
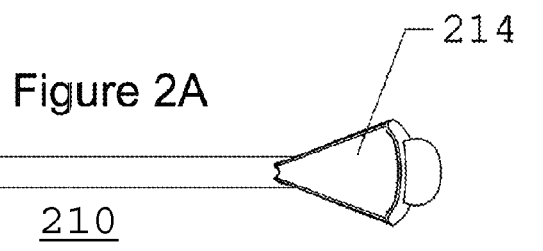
FIG. 2a is a bottom elevation view of a combination tongue and flap retractor with an S-shaped bend, where the flap retractor is at a reduced angle with respect to the handle axis and a more sharply curved tongue retractor in accordance with an embodiment of the present invention.
Figure 2B:
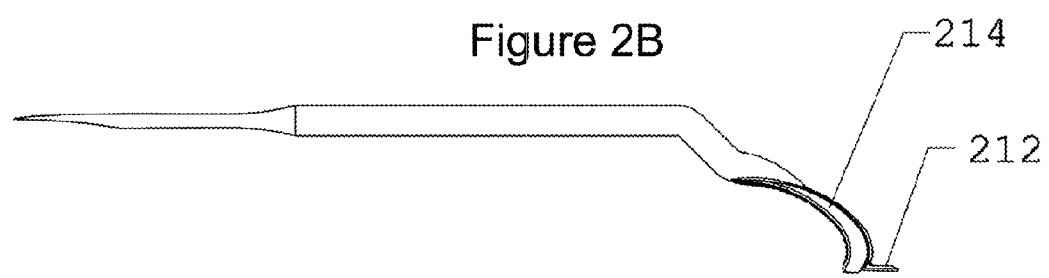
Figure 2C:
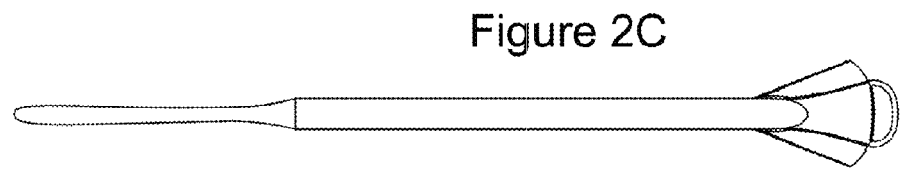
Figure 2D:
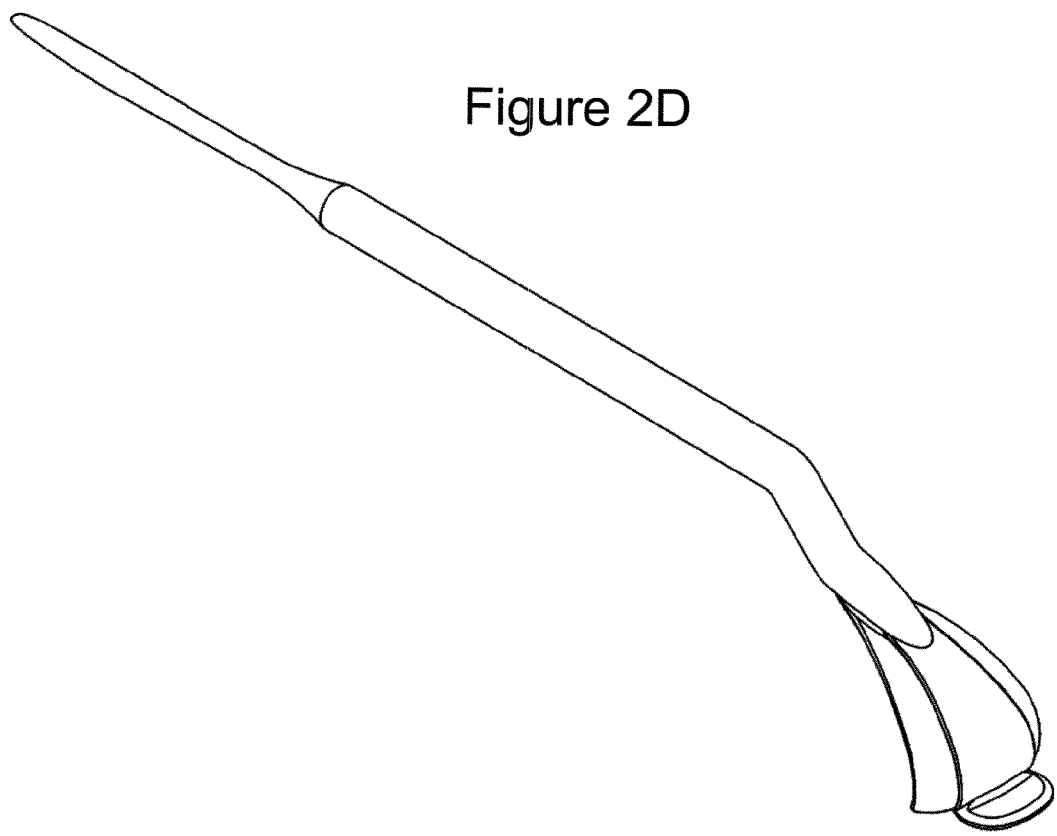
Figure 2E:
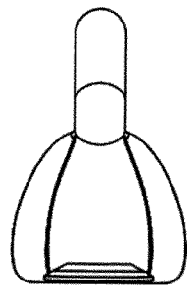
Figure 2F:
Figure 3A:
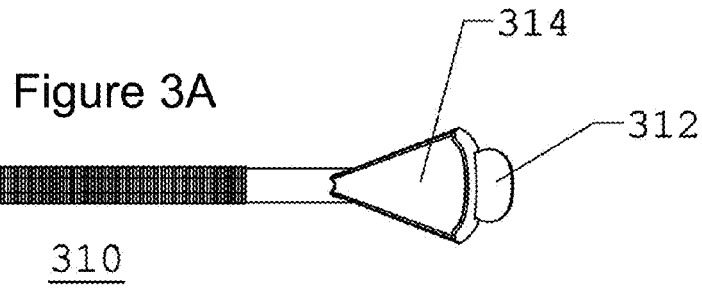
FIG. 3a is a bottom elevation view of a combination tongue and flap retractor with an S-shaped bend where the flap retractor is at a greater angle with respect to the handle axis, and a concave tongue retractor in accordance with an embodiment of the present invention.
Figure 3B:
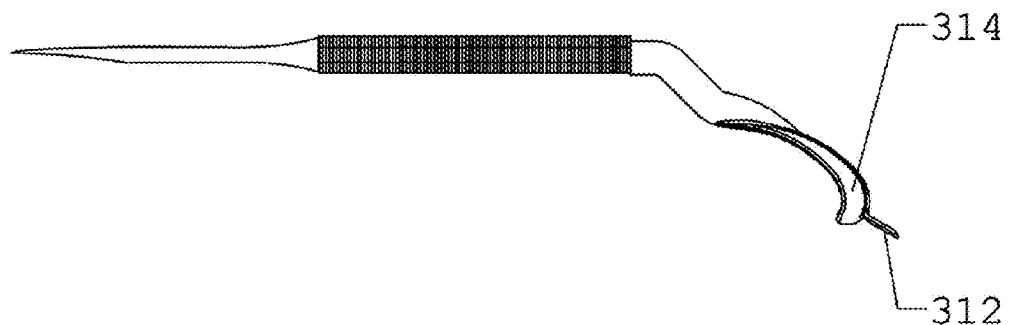
Figure 3C:
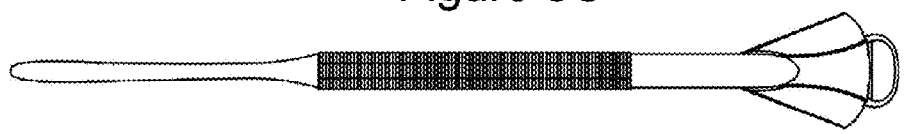
Figure 3D:
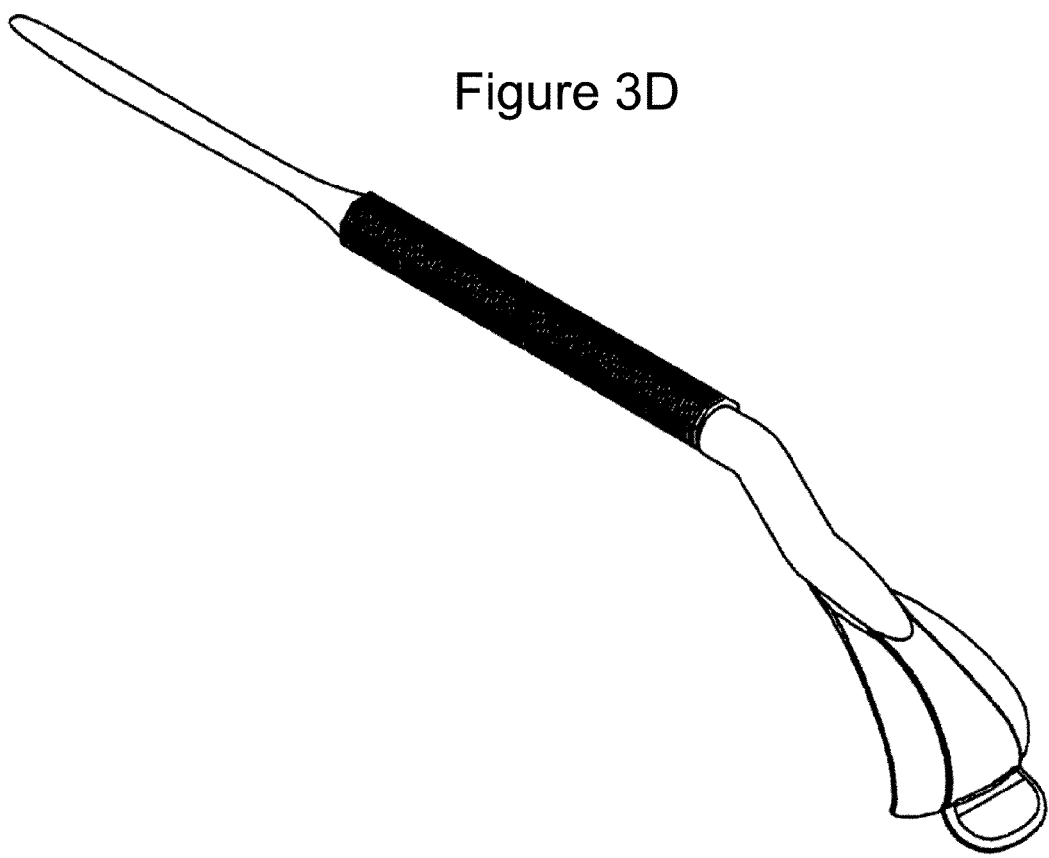
Figure 3E:
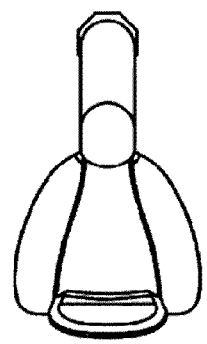
Figure 3F:

FIG. 3a shows another embodiment 310 in which the tongue retractor 314 may be located on a different plane than the flap retractor. As can be appreciated by comparing FIGS. 2b and 3b, the angle of the flap retractor may be varied with respect to the central axis of the handle. While the flap retractor 212 of FIG. 2b is disposed at a relatively shallow angle with respect to the central axis of the handle, the flap retractor 312 of FIG. 3b is disposed at a steeper angle. In general, this angle may range from zero degrees to almost 90 degrees. Moreover, the tongue retractor may also have the flap retractor positioned in generally the same plane as the tongue retractor.

Figure 4A:
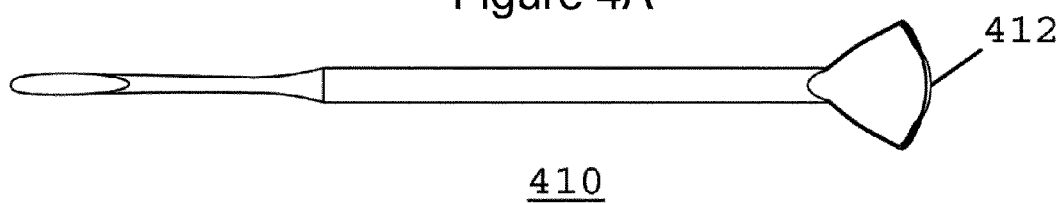
FIG. 4a is a bottom elevation view of a combination tongue and flap retractor with the tongue and flap retractor disposed on the same plane, with an S-shaped bend, and a short flap retractor in accordance with an embodiment of the present invention.
Figure 4B:
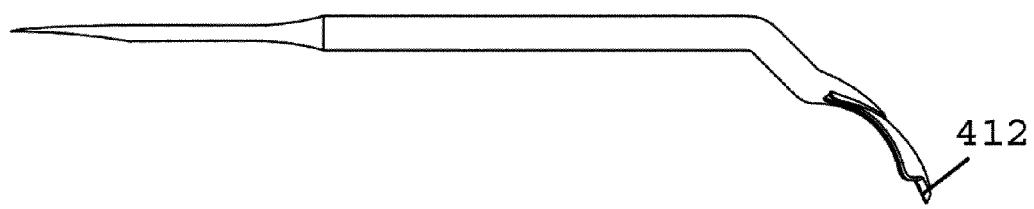
Figure 4C:
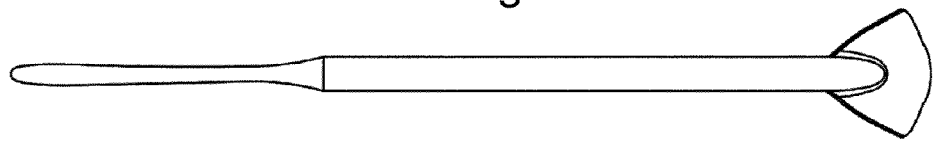
Figure 4D:
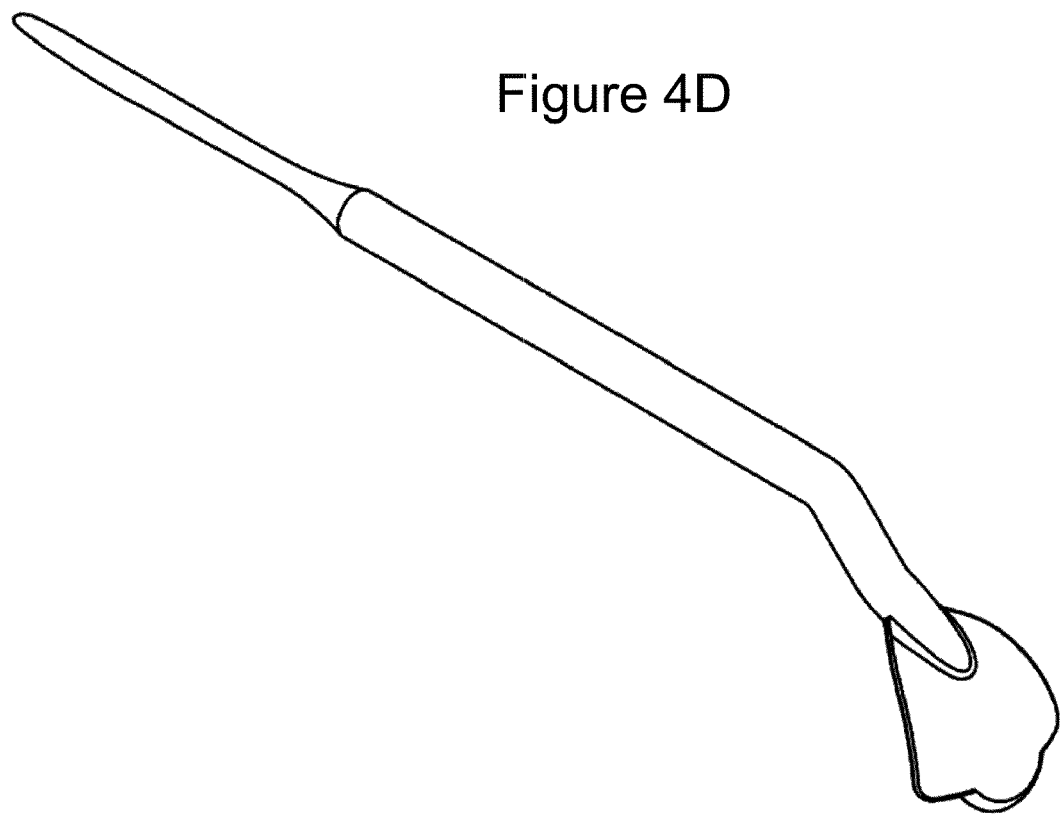
Figure 4E:
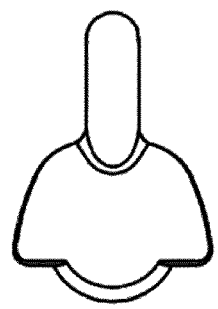
Figure 4F:
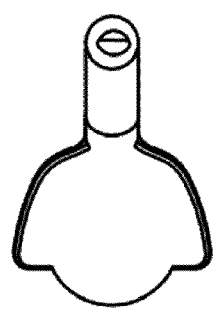

Thus, in one embodiment of the present invention, the concave tongue retractor and the flap retractor are integrated into a single instrument, a combination tongue and flap retractor. In addition, the flap retractor is in the form of a tapered, extended edge or tab, which can be made in various lengths. By way of illustration, FIG. 4a illustrates a concave tongue and flap retractor 410, similar to that of FIG. 1a, except that it includes a shortened flap retractor 412 as compared to flap retractor 112. The shortened flap retractor 412 may be useful when the flap being manipulated is not a large one.

Figure 5A:
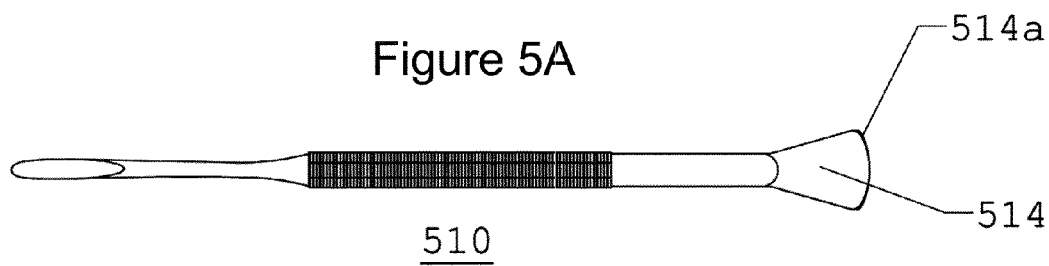
FIG. 5a is a bottom elevation view of a combination tongue and flap retractor with an S-shaped bend, and a thickened tongue and flap retractor both formed as a continuous planar extension in accordance with an embodiment of the present invention.
Figure 5B:
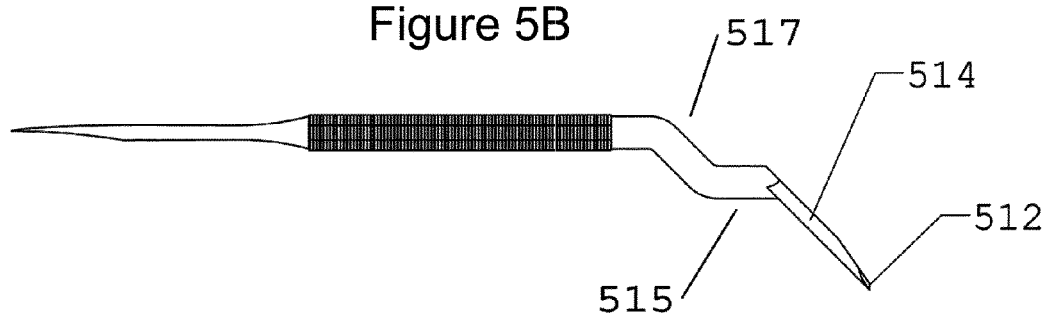
Figure 5C:
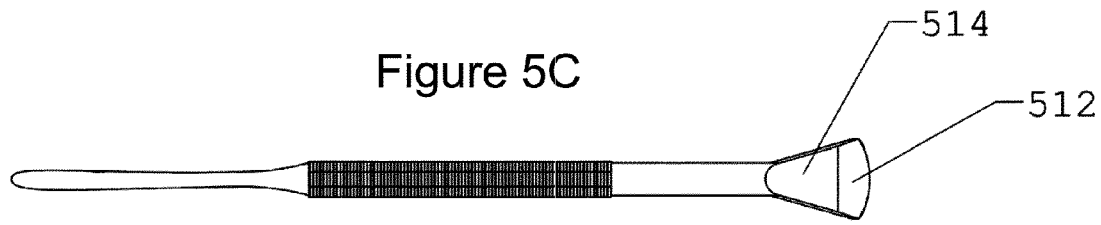
Figure 5D:
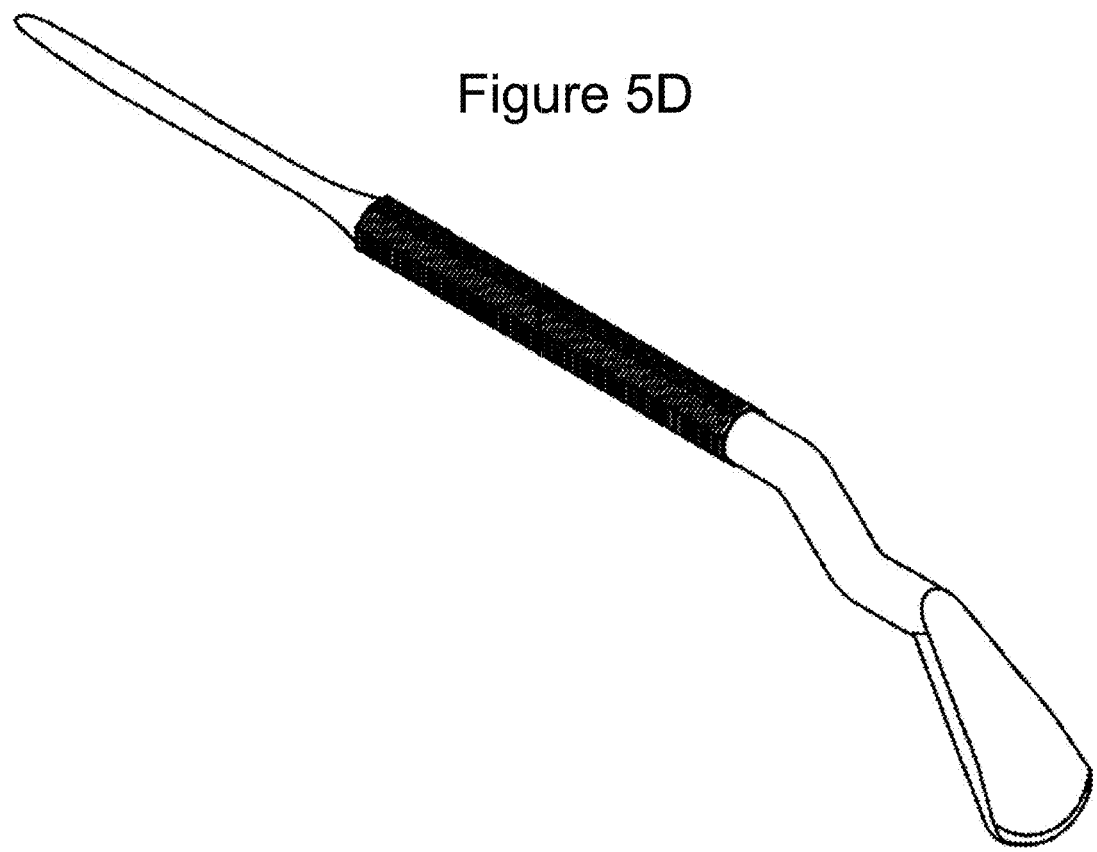
Figure 5E:
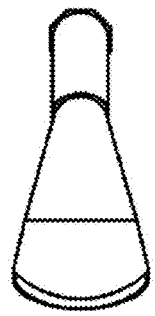
Figure 5F:
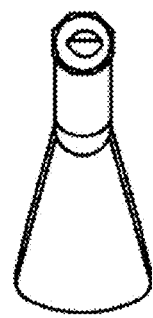

Yet another embodiment of the present invention is directed to an integrated non-concave tongue and flap retractor as shown in FIG. 5a. This combination tongue and flap retractor provides the same advantages as the combination tongue and flap retractor of the previous embodiments discussed above, but provides yet another option for the Dentist. Instead of the concave tongue retractor described above, the flap and tongue retractor 510 is provided with a greater thickness 514 relative to standard dental instruments, and is intended to be inserted into the oral cavity where the flap refraction is provided by a tapered leading edge 512 of the retractor 514. This device also incorporates specifically rounded corners 514a to better fit into the rounded shape of the mandible. The increased thickness portion 514 may be as little as a few tenths of a millimeter in thickness to several millimeters or more. For example, the thickness can be at least 0.5 millimeters. The integrated non-concave tongue and flap refractor 510 also includes the S-shaped bend 517 in the neck region 515 for better ergonomics and advantages as described herein.

Figure 6A:
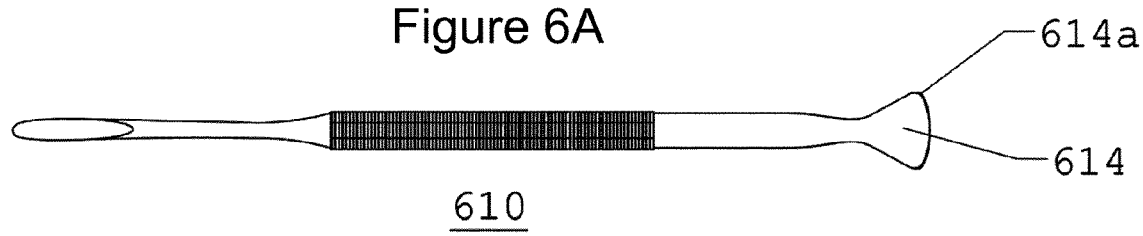
FIG. 6a is a bottom elevation view of a combination tongue and flap retractor with an S-shaped bend, and a small, thin tongue and flap retractor both formed as a continuous planar extension in accordance with an embodiment of the present invention.
Figure 6B:
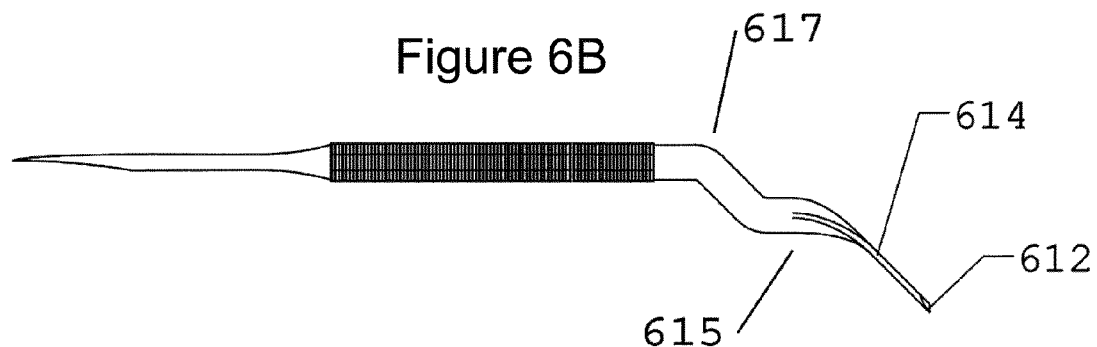
Figure 6C:

As can be further appreciated from FIG. 6a, the integrated non-concave tongue and flap retractor may be formed in various sizes. FIG. 6a, for example, shows an integrated retractor 610, similar to that of FIG. 5a but smaller in size. Similar to the embodiment of FIG. 5a, the integrated retractor includes rounded corners 614a to better fit in the mandible and also includes the S-shaped bend 617 in the neck region 615 for better ergonomics and advantages as described herein. The integrated retractor 610, also includes a greater thickness 614 and a tapered leading edge 612 similar to that of FIG. 5a. The increased thickness portion 614 may be as little as a few tenths of a millimeter in thickness to several millimeters of more.

Figure 7A:
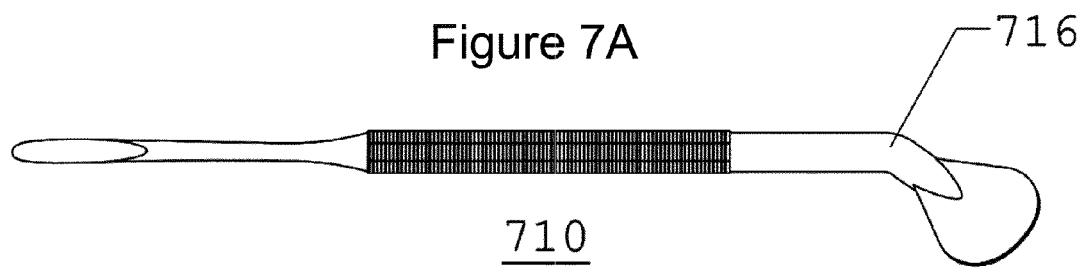
FIG. 7a is a bottom elevation view of a combination tongue and flap retractor with an S-shaped bend, bent to the left and thickened tongue and flap retractor both formed as a continuous planar extension in accordance with an embodiment of the present invention.
Figure 7B:
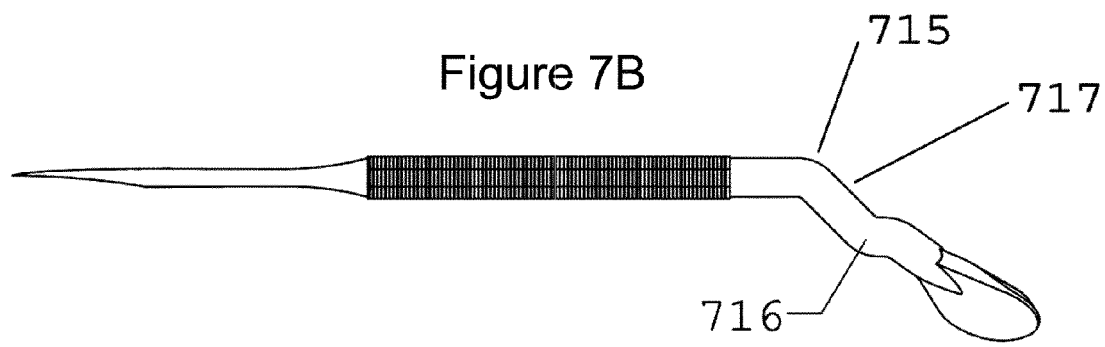
Figure 7C:
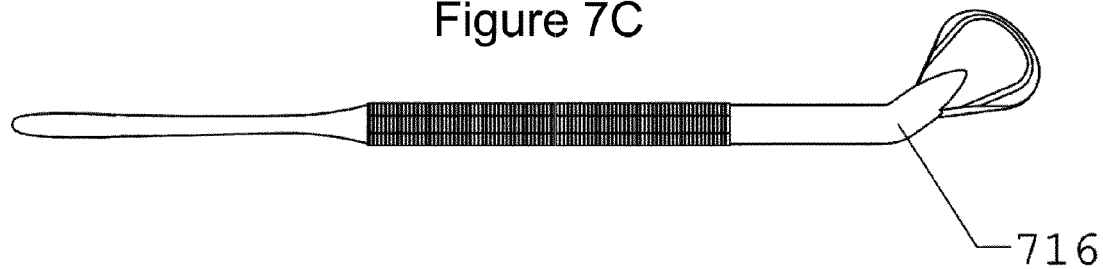
Figure 7D:
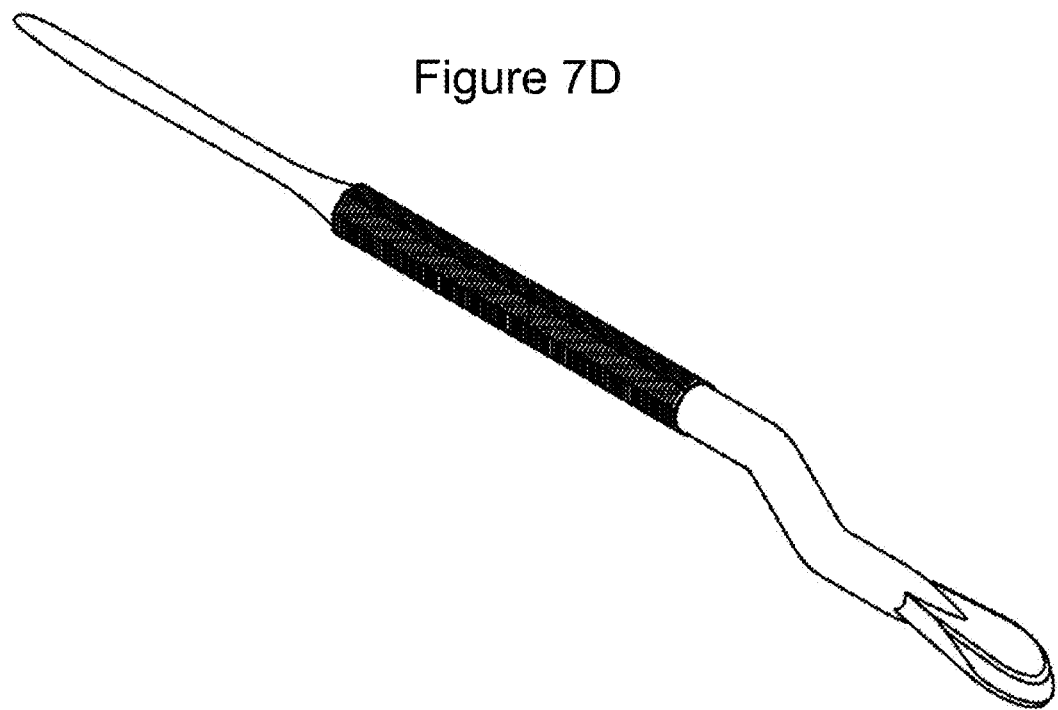
Figure 7E:
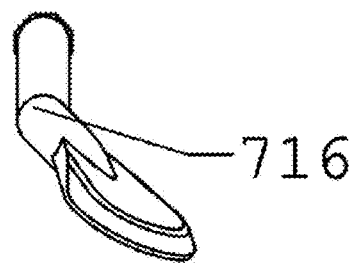
Figure 7F:
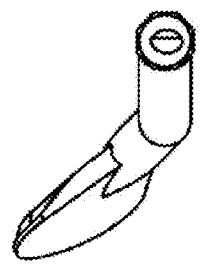

In one embodiment, the neck region may also include a lateral bend positioned at the proximal end of the operational unit, so as to position the operational unit either to the right or the left with respect to the central axis of the handle. As shown in FIG. 7a, the combination tongue and flap retractor 710 includes a bend 716, which may be useful in navigating the instrument on one particular side of the mandible. This design feature allows the Dentist to utilize the instrument in a dramatically less awkward fashion. Furthermore, this design allows the Dentist to reduce or eliminate the need for twisting or turning their torso, upper extremities, and head and neck in an effort to use the instrument. Thus, the risk of injury to the Dentist can also be reduced or eliminated. This embodiment also includes the S-shaped bend 717 in the neck region 715 for better ergonomics and advantages as described herein.

Figure 8A:
FIG. 8a is a bottom elevation view of a concave tongue retractor with an S-shaped bend in accordance with an embodiment of the present invention.
Figure 8B:
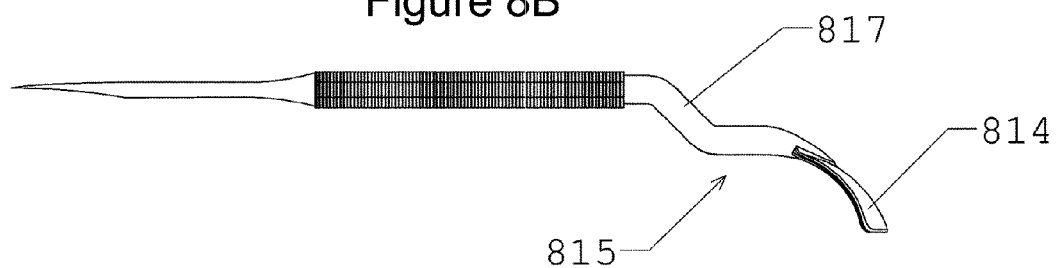
Figure 8C:
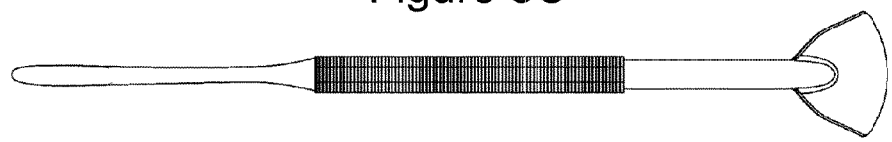

Though the previous embodiments have described tongue and flap retractors in combination, in another embodiment, the features of the tongue retractor disclosed above may be implemented without a flap retractor. FIG. 8a shows a straight concave tongue retractor 810 with a concave design 814 for tongue encapsulation without a flap retractor. The straight concave tongue retractor 810 also includes the S-shaped bend 817 in the neck region 815 for better ergonomics and advantages as described herein.

Figure 9A:
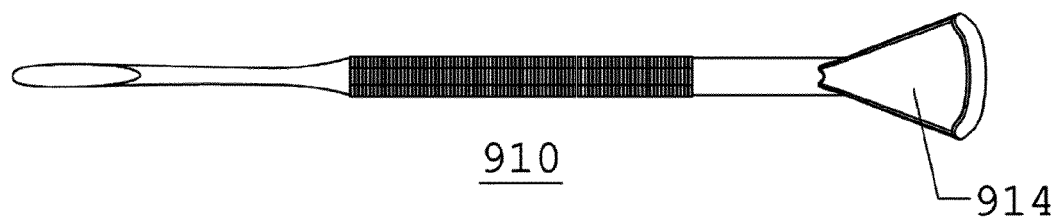
FIG. 9a is a bottom elevation view of a more sharply curved concave tongue retractor with an S-shaped bend in accordance with an embodiment of the present invention.
Figure 9B:
Figure 9C:
Figure 9D:
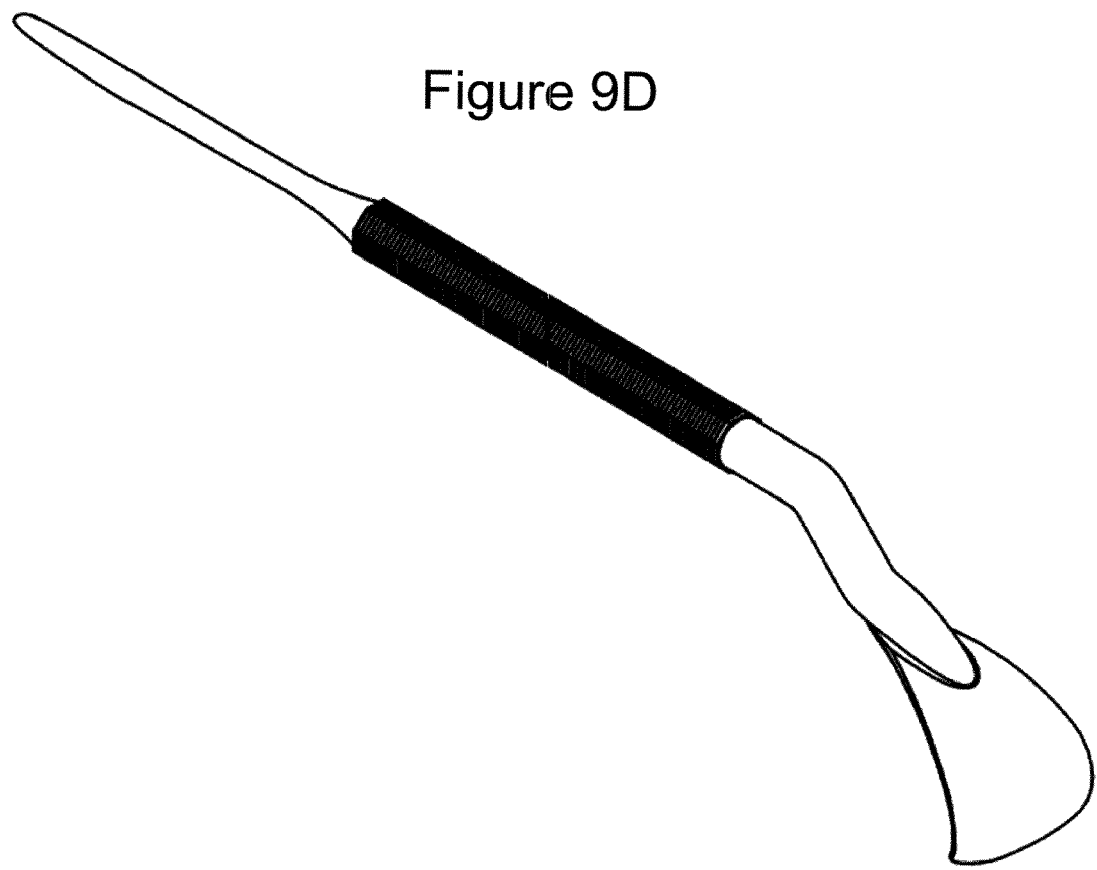
Figure 9E:
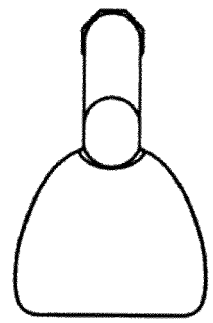
Figure 9F:
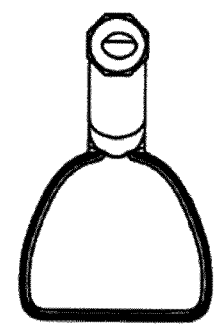

Likewise, FIG. 9a shows a concave tongue retractor 910 similar to the straight concave tongue retractor 810, but with a longer, and more sharply curved tongue retractor 914 for better encapsulation of the tongue. The concave tongue retractor 910 may be formed by sharply curving the distal portion of the tongue retractor 914.

Figure 10A:
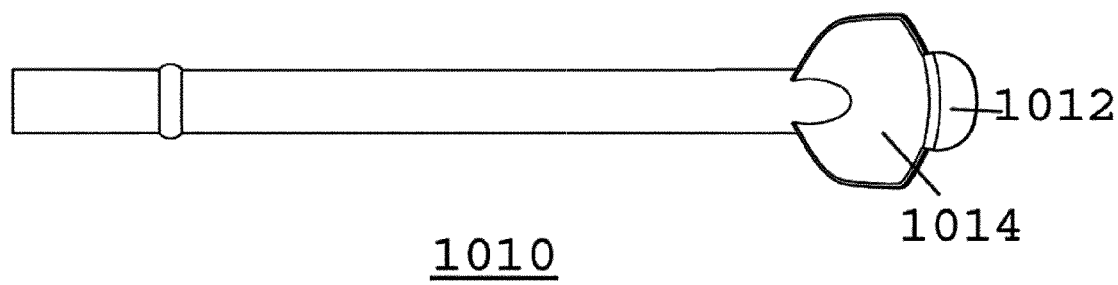
FIG. 10a is a bottom elevation view of a combination concave tongue and flap retractor with an S-shaped bend and a high speed suction device in accordance with an embodiment of the present invention.
Figure 10B:
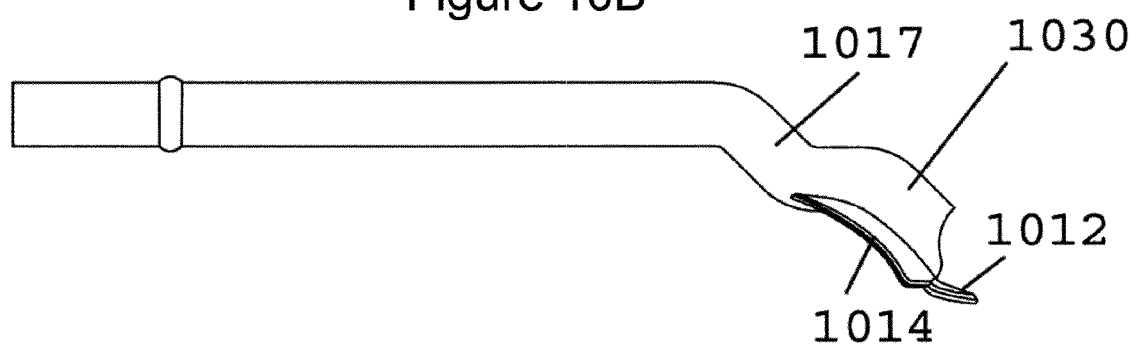
Figure 10C:
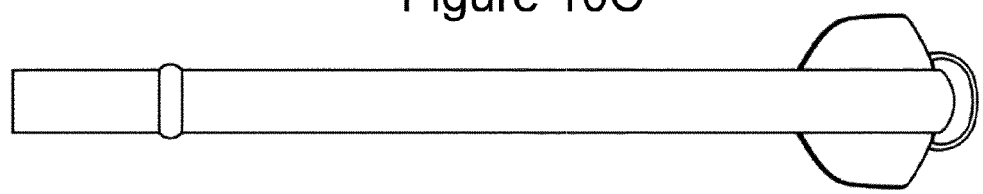
Figure 10D:
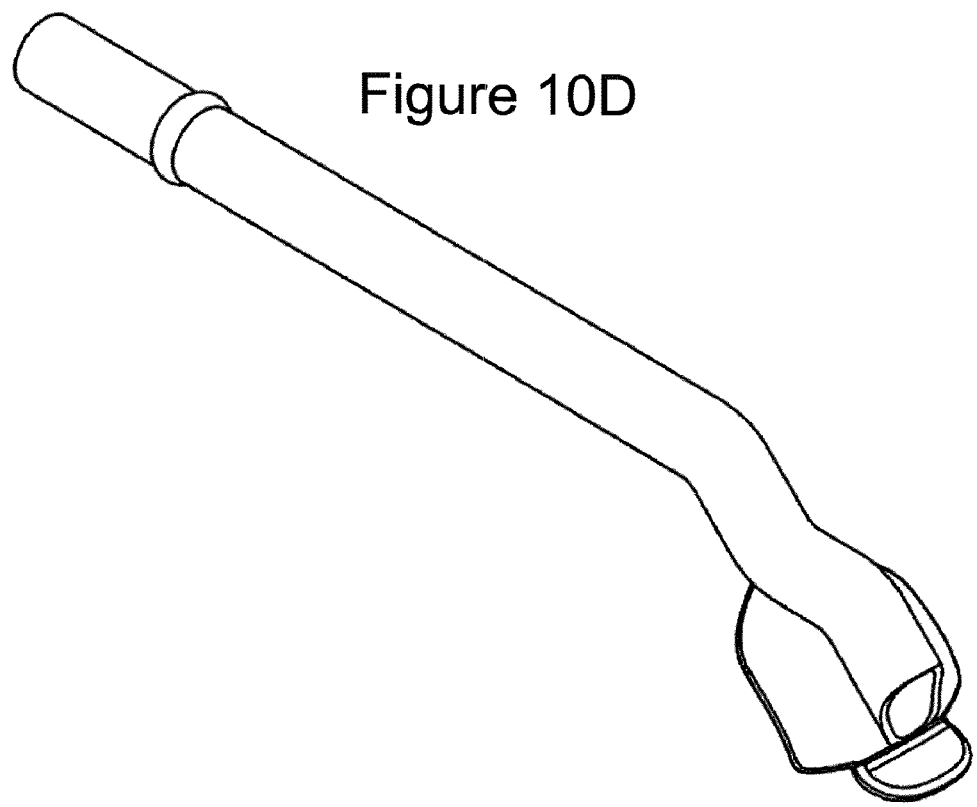
Figure 10E:
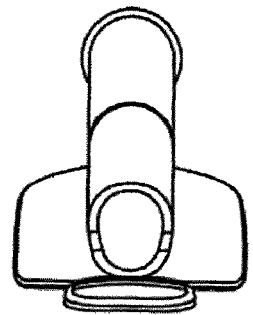
Figure 10F:
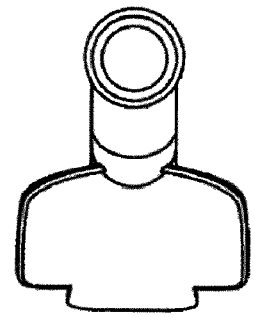

Finally, a high speed suction device may be incorporated in conjunction with any of the instruments disclosed herein. As shown in FIG. 10a, a high speed suction device 1010 includes many of the features described above. For example, the suction device 1010 includes a tongue retractor 1014, and a flap retractor 1012, as well as an S-shaped bend 1017. Furthermore, the suction device 1010 includes a suction shaft 1030 for eliminating fluids such as saliva, water, and blood from the oral cavity. The suction shaft may be in the form of a tube, duct or otherwise hollow body capable of eliminating fluids from the area of operation.

Thus, while there have been shown, described, and pointed out fundamental novel features of the invention as applied to several embodiments, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated.

What is claimed is:

1. A dental retractor, comprising:
an operational unit including a concave tongue retractor and a flap retractor, both retractors located at a distal end region of said operational unit, wherein the tongue retractor is disposed proximal to the flap retractor with the flap retractor being located on a convex surface of the tongue retractor at a most distal region of the dental retractor, the tongue retractor curved to be concave towards a proximal end of the operational unit and configured to encapsulate at least a portion of a tongue, and the flap retractor extending in a distal direction;
a neck region being connected to said operational unit at the proximal end of said operational unit; and
a handle region connected to said neck region at a proximal end of said neck region;
wherein the dental retractor is configured to retract the tongue and a gingival flap simultaneously.

2. The dental retractor of claim 1, wherein the flap retractor has a longitudinal dimension and a lateral dimension, wherein the longitudinal dimension of the flap retractor is in the range of 10-90% of the lateral dimension of the flap retractor.

3. The dental retractor of claim 1, wherein the neck region contains an S-shaped bend.

4. The dental retractor of claim 1, wherein the neck region comprises a lateral bend.

5. The dental retractor of claim 1, wherein the flap retractor comprises a beveled edge.

6. The dental retractor of claim 1, wherein the dental retractor is a unitary structure.

7. The dental retractor of claim 1, wherein the dental retractor is formed of at least two connected segments.

8. The dental retractor of claim 1, further comprising a suction shaft.

9. The dental retractor of claim 1, wherein the handle region includes a faceted cross sectional shape.

10. A dental tool, comprising:
a handle;
a tongue retractor coupled to the handle at a first end of the tongue retractor, the tongue retractor comprising a concave surface configured to encapsulate at least a portion of a tongue and a convex surface; and
a flap retractor directly connected to the convex surface at a second end of the tongue retractor that is substantially opposite the first end of the tongue retractor, the flap retractor extending away from the convex surface of the tongue retractor and configured to retract a gingival flap;
wherein the dental tool is configured to retract the tongue and the gingival flap simultaneously.

11. The dental tool of claim 10 further comprising an S-shaped neck disposed between the handle and the tongue retractor.

12. The dental tool of claim 11, wherein the neck further comprises a lateral bend.

13. A dental tool, comprising:
a handle;
a tongue retractor configured to encapsulate at least a portion of a tongue coupled to the handle at a first end of the tongue retractor, the tongue retractor is curved to form a concave surface and a convex surface; and
a flap retractor configured to retract a gingival flap connected to and extending from the tongue retractor at a second end of the tongue retractor substantially opposite the first end of the tongue retractor, the flap retractor angled away from the first end of the tongue retractor, wherein the dental tool is configured to retract the tongue and the gingival flap simultaneously.

14. The dental tool of claim 13 wherein the flap retractor is directly connected to an edge of the tongue retractor.

15. The dental tool of claim 13 wherein the flap retractor is directly connected to the convex surface of the tongue retractor.

16. The dental tool of claim 13 further comprising an S-shaped neck disposed between the handle and the tongue retractor.

17. The dental tool of claim 16, wherein the neck further comprises a lateral bend.

* * * * *